United States Patent
Chen et al.

(10) Patent No.: US 12,096,988 B2
(45) Date of Patent: Sep. 24, 2024

(54) METHOD AND SYSTEM OF DETERMINING OPERATION PATHWAY BASED ON IMAGE MATCHING

(71) Applicant: BRAIN NAVI BIOTECHNOLOGY CO., Zhubei (TW)

(72) Inventors: Chieh Hsiao Chen, Santa Clara, CA (US); Kuan Ju Wang, Santa Clara, CA (US)

(73) Assignee: BRAIN NAVI BIOTECHNOLOGY CO., LTD., Zhubei (TW)

( * ) Notice: Subject to any disclaimer, the term of this patent is extended or adjusted under 35 U.S.C. 154(b) by 505 days.

(21) Appl. No.: 17/436,028

(22) PCT Filed: Mar. 19, 2020

(86) PCT No.: PCT/CN2020/080194
§ 371 (c)(1),
(2) Date: Sep. 2, 2021

(87) PCT Pub. No.: WO2020/187289
PCT Pub. Date: Sep. 24, 2020

(65) Prior Publication Data
US 2022/0175454 A1    Jun. 9, 2022

Related U.S. Application Data (60) Provisional application No. 62/820,804, filed on Mar. 19, 2019.

(51) Int. Cl.
*A61B 34/10*    (2016.01)
*A61B 34/30*    (2016.01)
(Continued)

(52) U.S. Cl.
CPC .............. *A61B 34/10* (2016.02); *A61B 34/30* (2016.02); *A61B 90/36* (2016.02); *G06T 7/344* (2017.01);
(Continued)

(58) Field of Classification Search
CPC ......... A61B 34/10; A61B 34/30; A61B 90/36; A61B 2034/105; A61B 2034/107;
(Continued)

(56) References Cited

U.S. PATENT DOCUMENTS

| | | | |
|---|---|---|---|
| 9,437,003 B2 * | 9/2016 | Park | ........................... G06T 7/74 |
| 9,600,138 B2 * | 3/2017 | Thomas | .................. G06T 19/20 |

(Continued)

FOREIGN PATENT DOCUMENTS

| | | |
|---|---|---|
| CN | 101862220 A | 10/2010 |
| CN | 104083217 A | 10/2014 |

(Continued)

OTHER PUBLICATIONS

International Search Report and Written Opinion dated Jun. 19, 2020 from the International Application PCT/CN2020/080194.
(Continued)

*Primary Examiner* — Vijay Shankar
(74) *Attorney, Agent, or Firm* — Haverstock & Owens, A Law Corporation (57) ABSTRACT

Embodiments of the present disclosure set forth a method to determine an operation pathway for a patient. The method includes constructing a three-dimensional model of the patient; obtaining image information of the patient; selecting a first set of two-dimensional feature points associated with the three-dimensional model and a second set of two-dimensional feature points associated with the image information; transforming the first set of two-dimensional feature points to a first set of three-dimensional feature points and
(Continued)

the second set of two-dimensional feature points to a second set of three-dimensional feature points, respectively; matching between the first set of three-dimensional feature points and the second set of three-dimensional feature points to determine a relationship that aligns the first set of three-dimensional feature points and the second set of three-dimensional feature points; and determining the operation pathway in a coordinate system associated with a robotic arm.

16 Claims, 9 Drawing Sheets

(51) Int. Cl.
 *A61B 90/00* (2016.01)
 *G06T 7/33* (2017.01)
 *G06T 7/73* (2017.01)
(52) U.S. Cl.
 CPC .......... *G06T 7/75* (2017.01); *A61B 2034/105* (2016.02); *A61B 2034/107* (2016.02); *A61B 2090/367* (2016.02); *G06T 2207/30016* (2013.01)
(58) Field of Classification Search
 CPC ............ A61B 2090/367; A61B 90/361; A61B 2090/371; A61B 34/20; A61B 2034/2065; G06F 3/011; G06F 3/015; G06T 7/344; G06T 7/75; G06T 2207/30016; G06T 2207/10072
 See application file for complete search history.

(56) References Cited

U.S. PATENT DOCUMENTS

| | | | | |
|---|---|---|---|---|
| 9,827,053 | B2* | 11/2017 | Chen | ..................... G06T 7/73 |
| 11,648,066 | B2* | 5/2023 | Chen | ..................... A61B 34/20 |
| | | | | 606/130 |
| 2014/0112529 | A1 | 4/2014 | Park et al. | |
| 2016/0070436 | A1* | 3/2016 | Thomas | ................ G06T 7/0012 |
| | | | | 715/771 |
| 2018/0092699 | A1 | 4/2018 | Finlay | |
| 2019/0142359 | A1* | 5/2019 | Zhang | ................... A61B 34/20 |
| | | | | 606/130 |

FOREIGN PATENT DOCUMENTS

| | | |
|---|---|---|
| CN | 106794044 B | 9/2019 |
| CN | 107468350 | 12/2020 |
| CN | 107468350 B | 12/2020 |
| EP | 3145420 B1 | 3/2016 |
| JP | 2015-198893 A | 11/2015 |
| TW | 201622660 A | 7/2016 |
| TW | 201705078 A | 2/2017 |
| TW | 201907366 A | 2/2019 |
| WO | 2014194167 A1 | 12/2014 |
| WO | 2016126934 A1 | 8/2016 |
| WO | 2018223925 A1 | 12/2018 |

OTHER PUBLICATIONS

Korean Application Examination Opinion, Application No. 10-2021-7031085, dated Jul. 31, 2023.
Japanese Application No. 2021-556512, 1st Examination Opinion.
Japanese Application No. 2021-556512, 2nd Examination Opinion.
Indian Application Examination Opinion, Application No. 202127042558, dated: Mar. 29, 2022.
Extended European Search Report , Application No. 20774642.1, dated Aug. 12, 2022.
Chinese Examination Opinion, Application No. 202080022953.1, dated May 6, 2023.
Chinese Application Search Report, Application No. 2020800229531, dated Mar. 19, 2020.
Canadian Application Examination Opinion, Application No. 3,134,069, dated Dec. 19, 2022.
Taiwanese Application Examination Opinion, Application No. 11020588140, dated Jun. 23, 2023.
Taiwanese Application Search Report, 109109049, dated Mar. 19, 2019.

* cited by examiner

METHOD AND SYSTEM OF DETERMINING OPERATION PATHWAY BASED ON IMAGE MATCHING

CROSS-REFERENCE TO RELATED APPLICATIONS

This application claims the benefit of U.S. Provisional Application No. 62/820,804, filed Mar. 19, 2019, which is incorporated by reference in its entirety.

BACKGROUND OF THE INVENTION

Field of the Invention

Embodiments of the present invention relate generally to methods and systems of determining one or more points on an operation pathway.

Description of the Related Art

Unless otherwise indicated herein, the approaches described in this section are not prior art to the claims in this application and are not admitted to be prior art by inclusion in this section.

In an operation, a plan of an operation pathway is critical. The operation pathway may include multiple points, such as a safety point and a preoperative point away from the patient, an entry point on patient's tissues, and a target point at the target of the operation.

Robotic operation may offer a precise control of the operation pathway. Before the operation, patient is subjected to a medical scan (e.g., CT, MRI, PET, ultrasound etc.). The operation pathway to the desired anatomical region is planned. Artificial intelligence may be employed to suggest optimal routes with minimal damages to the surgeon. To perform the operation, the position of the patient may be matched to the perspective of the medical scan to accurate perform the operation along the planned operation pathway. Conventional approaches have relied on glued on or screwed in fiducial marks, which have not been widely adopted.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated herein.

Figure 1:
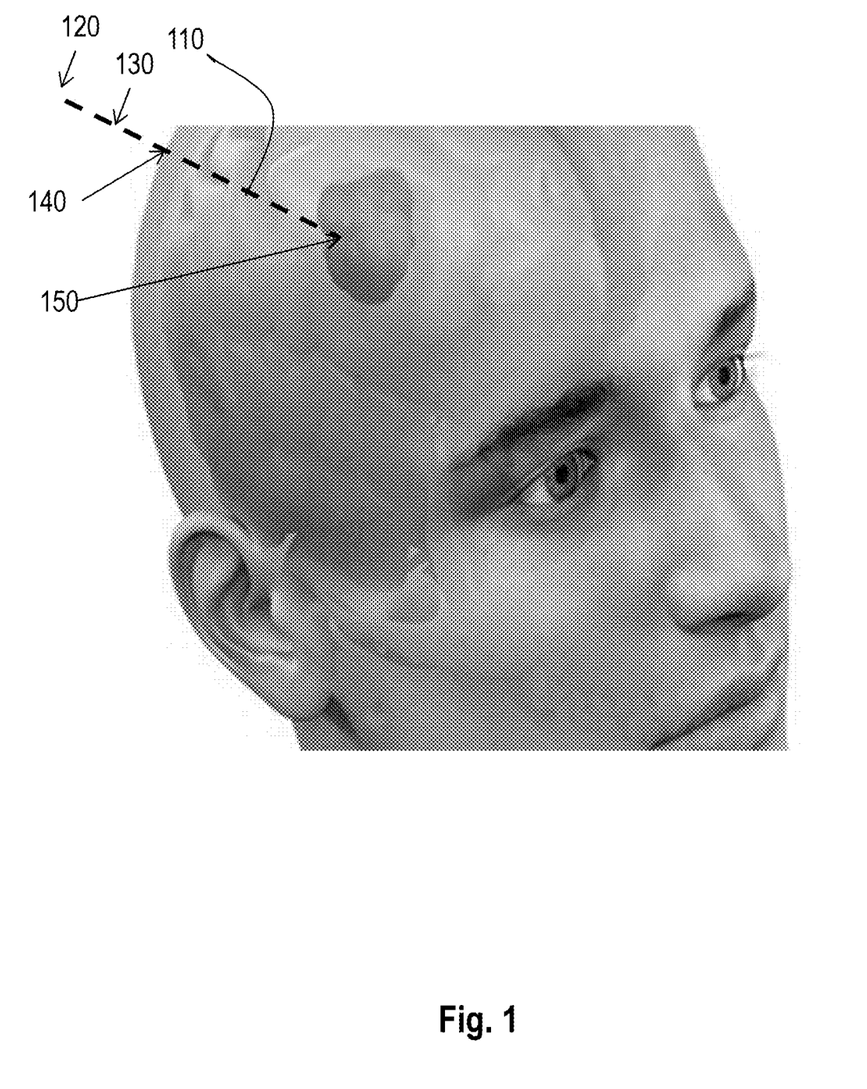
FIG. 1 is an example figure showing the spatial relationships among several points that may be encountered during an operation.

FIG. 1 is an example figure showing the spatial relationships among several points that may be encountered during an operation, arranged in accordance with some embodiments of the present disclosure. In FIG. 1, an operation pathway 110 may include safety point 120, preoperative point 130, entry point 140, and target point 150.

Figure 2:
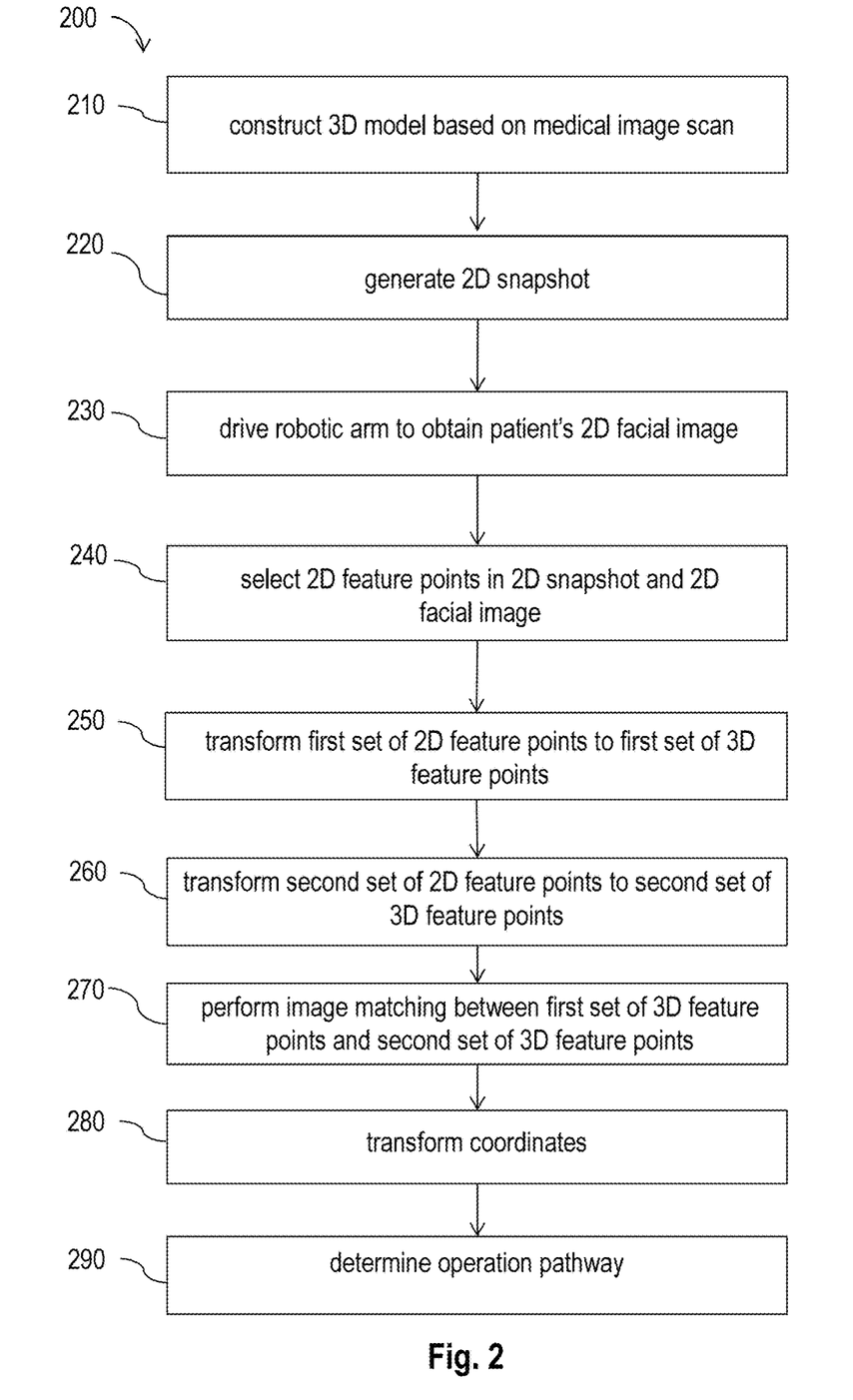
FIG. 2 is a flow diagram illustrating an example process to determine an operation pathway for a patient.

FIG. 2 is a flow diagram illustrating an example process 200 to determine an operation pathway for a patient, arranged in accordance with some embodiments of the present disclosure. Process 200 may include one or more operations, functions, or actions as illustrated by blocks 210, 220, 230, 240, 250, 260, 270, 280, and/or 290, which may be performed by hardware, software and/or firmware. The various blocks are not intended to be limiting to the described embodiments. The outlined steps and operations are only provided as examples, and some of the steps and operations may be optional, combined into fewer steps and operations, or expanded into additional steps and operations without detracting from the essence of the disclosed embodiments. Although the blocks are illustrated in a sequential order, these blocks may also be performed in parallel, and/or in a different order than those described herein.

Process 200 may begin at block 210, "construct 3D model based on medical image scan." Before an operation is performed, some medical imaging techniques may be used to capture a snapshot of a patient's conditions, so that an operation plan may be formulated. The operation plan may include a planned operation pathway as set forth above. For example, the surgeon may order a medical image scan (e.g., CT or MRI) of the operation target. Such a medical image scan may be performed a few days (e.g., 3 to 5 days) prior to the operation. A three-dimensional model may be constructed based on the medical image scan data using some known approaches. Accordingly, points on the planned operation pathway may be identified in the three-dimensional model.

Figure 3:
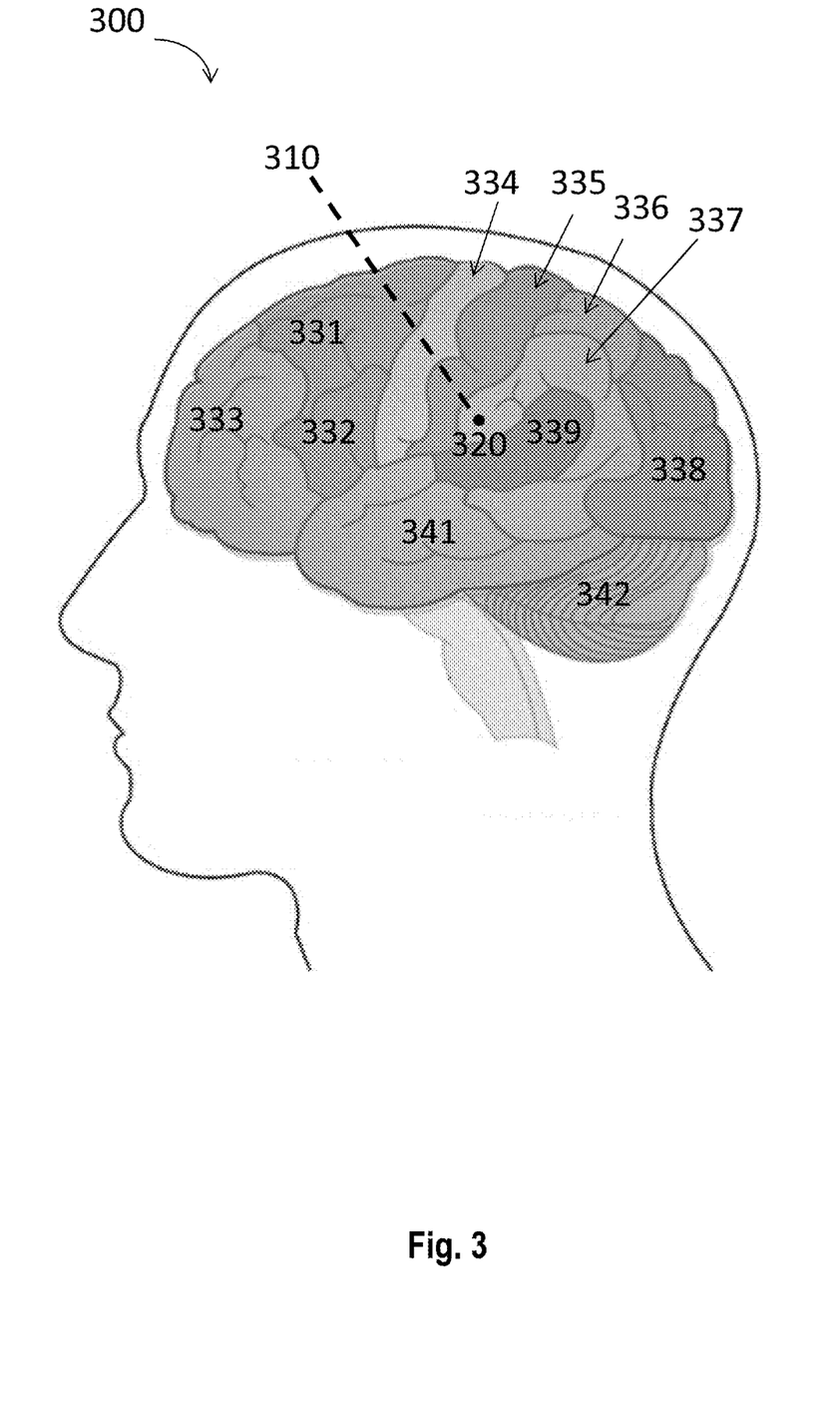
FIG. 3 illustrates an example of the operation pathway calculation.

In some embodiments, an artificial intelligence engine may be employed to suggest to the surgeon one or more planned operation pathways with minimal physical damages to the patient. Based on the patient's CT or MRI scan, the artificial intelligence engine may suggest one or more optimal planned operation pathways. FIG. 3 illustrates an example of calculating planned operation pathway 310 to reach target point 320, arranged in accordance with some embodiments of the present disclosure. The calculation may include transforming the standard brain-atlas data, and registering it to the patient's medical scan images to identify the brain regions. Some example brain regions include motor association area 331, expressive speech area 332, higher mental functions area 333, motor area 334, sensory area 335, somatosensory association area 336, global language area 337, vision area 338, receptive speech area 338, receptive speech area 339, association area 341, and cerebellum area 342. Moreover, common target tissues, such as sub-thalamic nucleus, may be automatically identified. In addition, each brain region set forth above may be assigned with a cost function for the artificial intelligence engine to suggest one or more planned operation pathways to the target tissues. The blood vessels may be identified from the TOF (time-of-flight MRI) data. The points on the outer brain boundary are candidate for entry point.

Block 210 may be followed by block 220 "generate 2D snapshot." In some embodiments, a two-dimensional snapshot is generated based on the three-dimensional model constructed in block 210. In some embodiments, the two-dimensional snapshot is a front view of the three-dimensional model of the patient. The front view of the patient includes at least some facial features of the patient.

Block 220 may be followed by block 230 "drive robotic arm to obtain patient's 2D facial image." In some embodiments, at least two two-dimensional optical devices (e.g., cameras and/or scanners) are fixed on the robotic arm. By driving the robotic arm to different positions, the two two-dimensional optical devices may capture different images associated with the patient. In some embodiments, each of the two two-dimensional optical devices is configured to collect two-dimensional images associated with the patient. In some other embodiments, the two two-dimensional optical devices, in combination, are configured to collect a depth information associated with the patient. Therefore, the at least two two-dimensional optical devices may collect either two-dimensional images associated with the patient or three-dimensional images associated with the patient.

Figure 4A:
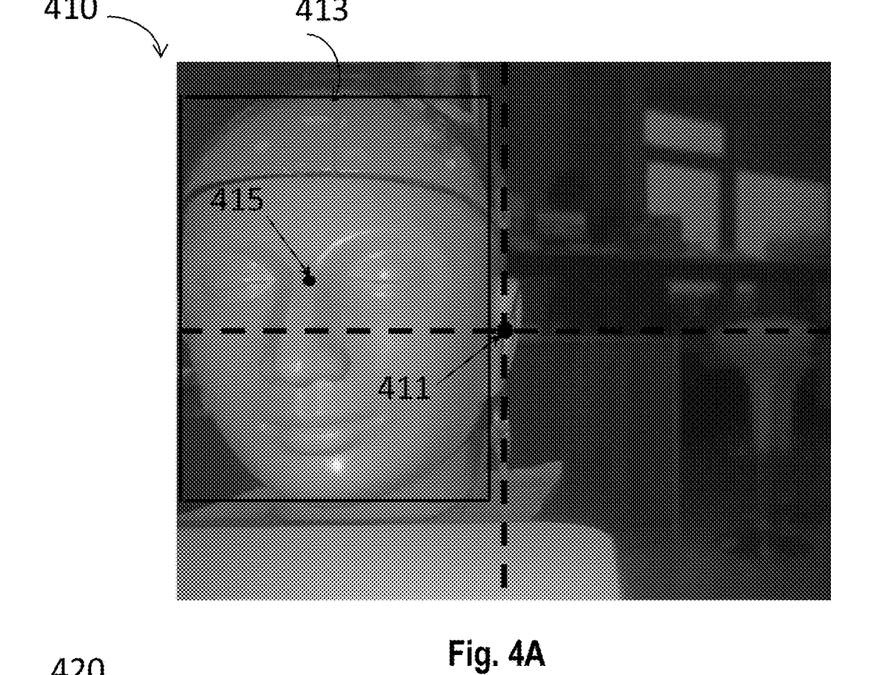
FIG. 4A is a two-dimensional image associated with the patient collected at a first time.

In conjunction with FIG. 4A, image 410 is a two-dimensional image associated with the patient collected at a first time. Image 410 has image center 411 with a coordinate (X, Y). An artificial intelligence engine may be employed to identify the patient in image 410. In some embodiments, the artificial intelligence engine may identify the patient in frame 413 in image 410. In addition, the artificial intelligence engine may identify facial central point 415 of the patient in image 410. Facial central point 415 may have a coordinate (x, y). In some embodiments, the robotic arm is driven at least based on a first offset of (X-x) and a second offset of (Y-y).

For example, at the first time, either the first offset or the second offset is greater than one or more predetermined thresholds, and the robotic arm is driven to another position to decrease the first offset and the second offset.

Figure 4B:
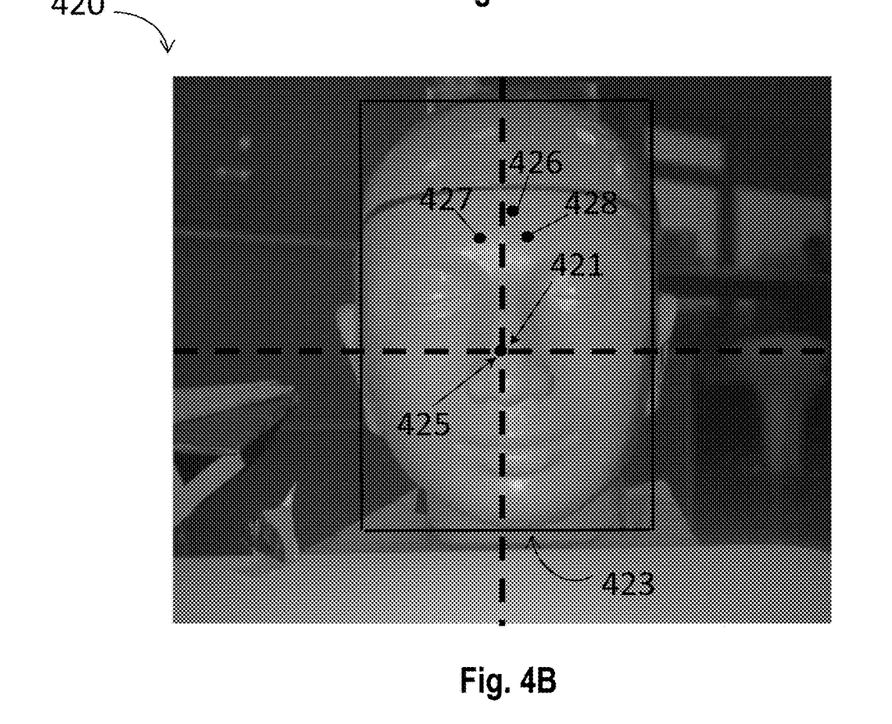
FIG. 4B is a two-dimensional image associated with the patient collected at a second time.

In some embodiments, in response to the robotic arm being driven to a first updated position at a second time, in conjunction with FIG. 4B, image 420 is a two-dimensional image associated with the patient collected by the two-dimensional optical devices on the robotic arm. Image 420 has an image center 421 with an updated coordinate (X, Y). An artificial intelligence engine may be employed to identify the patient in image 420. In some embodiments, the artificial intelligence engine may identify the patient in frame 423 in image 420. In addition, the artificial intelligence engine may identify a facial central point 425 of the patient in image 420. Facial central point 425 may have an updated coordinate (x, y). In some embodiments, the first offset of (X-x) and the second offset (Y-y) are both less than the one or more predetermined thresholds.

In some embodiments, at the first updated position at a third time, an artificial intelligence engine may be employed to identify at least three feature points 426, 427 and 428. The two-dimensional optical devices are configured to collect the depth information associated with the patient. The depth information may be assigned to feature points 426, 427 and 428, which can define a first plane in a three-dimensional space. In some embodiments, the robotic arm is driven to rotate and move to a second updated position at a fourth time so that the two-dimensional optical devices on the robotic arm is on a second plane substantially in parallel to the first plane in the three-dimensional space. In response to an average depth of image 420 at the second updated position in a predetermined range associated with operational parameters of the two-dimensional optical devices, image 420 is taken as the patient's 2D facial image and method 200 goes to block 240.

In block 240 "select 2D feature points in 2D snapshot and 2D facial image," an artificial intelligence engine may be employed to select a first set of two-dimensional feature points in the two-dimensional snapshot generated in block 220 and a second set of two-dimensional feature points in the patient's two-dimensional facial image (e.g., image 420) taken in block 230.

Figure 5:
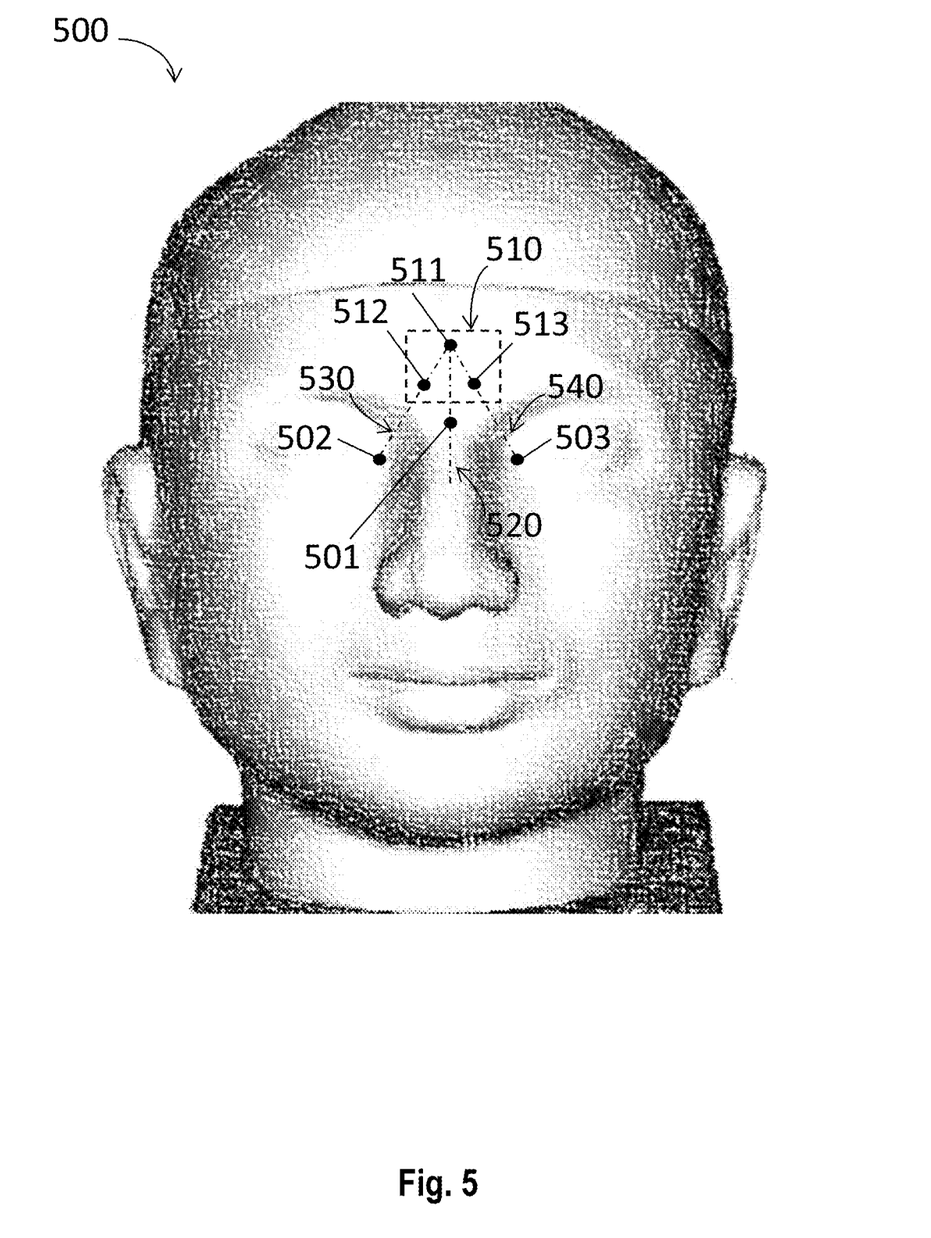
FIG. 5 is an image of a two-dimensional snapshot.

In conjunction with FIG. 5, image 500 is a two-dimensional snapshot generated in block 220. In some embodiments, an artificial intelligence engine may be employed to identify glabella 501, right endocanthion 502 and left endocanthion 503 as these points are easier to be identified in image 500. However, glabella 501, right endocanthion 502 and left endocanthion 503 may not be on the same two-dimensional plane for various races of people. Given image 500 is a two-dimensional snapshot, glabella 501, right endocanthion 502 and left endocanthion 503 are not suitable to be two-dimensional feature points on image 500. Nevertheless, based on anatomy, a small region 510 on faces of various races of people is statistically planar. Therefore, in some embodiments, the artificial intelligence engine is employed to generate three lines 520, 530 and 540 passing through glabella 501, right endocanthion 502 and left endocanthion 503, respectively and intersecting in region 510. In some embodiments, intersected point 511 is selected as a two-dimensional feature point. In addition, in some embodiments, point 512 in region 510 on line 530 and point 513 in region 510 on line 540 are also selected as two-dimensional feature points. Points 511, 512 and 513 may be a first set of two-dimensional feature points. In some embodiments, additional 2D points in region 510 may be selected to increase the number of the first set of two-dimensional feature points.

Figure 6:
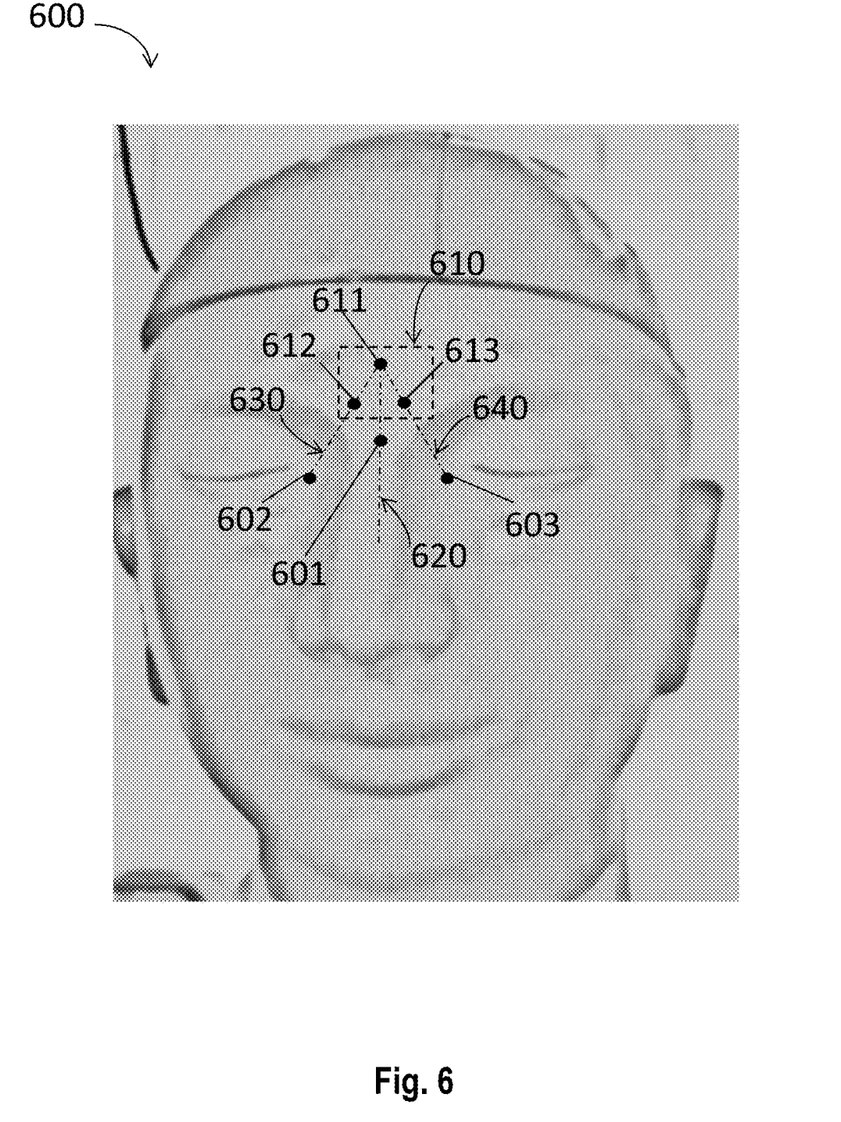
FIG. 6 is an image of a two-dimensional facial image.

In conjunction with FIG. 6, image 600 is a two-dimensional facial image taken in block 230. In some embodiments, an artificial intelligence engine may be employed to identify glabella 601, right endocanthion 602 and left endocanthion 603 as these points are easier to be identified in image 600. However, glabella 601, right endocanthion 602 and left endocanthion 603 may not be on the same two-dimensional plane for various races of people. Given image 600 is a two-dimensional facial image, glabella 601, right endocanthion 602 and left endocanthion 603 are not suitable to be two-dimensional feature points on image 600. Similarly, based on anatomy, a small region 610 on faces of various races of people is statistically planar. Nevertheless, in some embodiments, the artificial intelligence engine is employed to generate three lines 620, 630 and 640 passing through glabella 601, right endocanthion 602 and left endocanthion 603, respectively and intersecting in region 610. In some embodiments, the intersected point 611 is selected as a two-dimensional feature point. In addition, in some embodiments, a point 612 in region 610 on line 630 and a point 613 in region 610 on line 640 are also selected as two-dimensional feature points. Points 611, 612 and 613 may be a second set of two-dimensional feature points. In some embodiments, additional 2D points in region 610 may be selected to increase the number of the second set of two-dimensional feature points.

Block 240 may be followed by block 250 "transform first set of 2D feature points to first set of 3D feature points." In some embodiments, in block 250, the first set of two-dimensional feature points (e.g., points 511, 512 and 513) are transformed to a first set of three-dimensional feature points. As set forth above, the first set of two-dimensional feature points are selected in a two-dimensional snapshot generated in a constructed three-dimensional model. Based on the algorithm taken the two-dimensional snapshot in the constructed three-dimensional model, a reverse operation may be performed to transform the first set of two-dimensional feature points on the two-dimensional snapshot (e.g., snapshot generated in block 220) to a first set of three-dimensional feature points in the constructed three-dimensional model (e.g., three-dimensional model generated in block 210). In some embodiments, the first set of three-dimensional feature points may identify a first initial three-dimensional coordinate that allows subsequent matching using iterative closest point (ICP) algorithm.

Block 250 may be followed by block 260 "transform second set of 2D feature points to second set of 3D feature points." In some embodiments, in block 260, the second set of two-dimensional feature points (e.g., points 611, 612 and 613) are transformed to a second set of three-dimensional feature points. As set forth above, the depth information associated with the patient may be collected by the two-dimensional optical devices. In some embodiments, the depth information may be added to the second set of two-dimensional feature points to transform the second set of two-dimensional feature points to a second set of three-dimensional feature points. In some embodiments, the second set of three-dimensional feature points may identify a second initial three-dimensional coordinate that allows subsequent matching using iterative closest point (ICP) algorithm.

Block 260 may be followed by block 270 "perform image matching between first set of three-dimensional feature points and second set of three-dimensional feature points." In some embodiments, the first set of three-dimensional feature points and the second set of three-dimensional feature points are matched to determine a relationship that aligns the first set of three-dimensional feature points and the second set of three-dimensional feature points, sometimes iteratively to minimize the differences between the two sets of three-dimensional feature points.

For clarity, the following discussions mainly use one non-limiting example of the two two-dimensional optical devices (e.g., two two-dimensional cameras) and a three-dimensional coordinate system associated with the two two-dimensional optical devices, e.g., three-dimensional camera coordinate system, to explain various embodiments of the present disclosure.

Block 270 may be followed by block 280, "transform coordinates." In block 280, the first set of three-dimensional feature points in the constructed three-dimensional model are transformed from their original coordinate system (i.e., three-dimensional model coordinate system) to the coordinates of the images taken by the two two-dimensional optical devices (i.e., three-dimensional camera coordinate system). The transformation may be based on some image comparison approaches, such as iterative closest point (ICP). Block 280 may further include additional coordinate transformations in which all points on the three-dimensional camera coordinate system are transformed to the coordinates of the robotic arm (i.e., robotic arm coordinate system). The details of transforming coordinates will be further described below.

Block 280 may be followed by block 290, "determine operation pathway." In block 290, the coordinates of the planned operation pathway in three-dimensional model coordinate system may be transformed to the robotic arm coordinate system. Therefore, the robotic arm may move to the safety point, the preoperative point, the entry point, and/or the target point on the planned operation pathway.

In some embodiments, example process 200 may be applied to various types of operations, such as, without limitation, brain operations, nervous system operations, endocrine operations, eye operations, ears operations, respiratory operations, circulatory system operations, lymphatic operations, gastrointestinal operations, mouth and dental operations, urinary operations, reproductive operations, bone, cartilage and joint operations, muscle/soft tissue operations, breast operations, skin operations, and others.

In sum, at least two two-dimensional cameras or scanners may be used to obtain a patient's facial features. The facial features may then be compared with a two-dimensional snapshot of a three-dimensional model associated with a medical image scan. A first set of two-dimensional feature points are selected in the two-dimensional snapshot and a second set of two-dimensional feature points are selected in a two-dimensional patent's facial image obtained by the two-dimensional cameras or scanners, respectively. To compare, the first set of two-dimensional feature points and the second set of two-dimensional feature points are transformed to a first set of three-dimensional feature points in the three-dimensional model and a second set of three-dimensional feature points, respectively. In some embodiments, example process 200 may be applied to various types of operations, such as brain operations, nervous system operations, endocrine operations, eye operations, ears operations, respiratory operations, circulatory system operations, lymphatic operations, gastrointestinal operations, mouth and dental operations, urinary operations, reproductive operations, bone, cartilage and joint operations, muscle/soft tissue operations, breast operations, skin operations, and etc.

Figure 7:
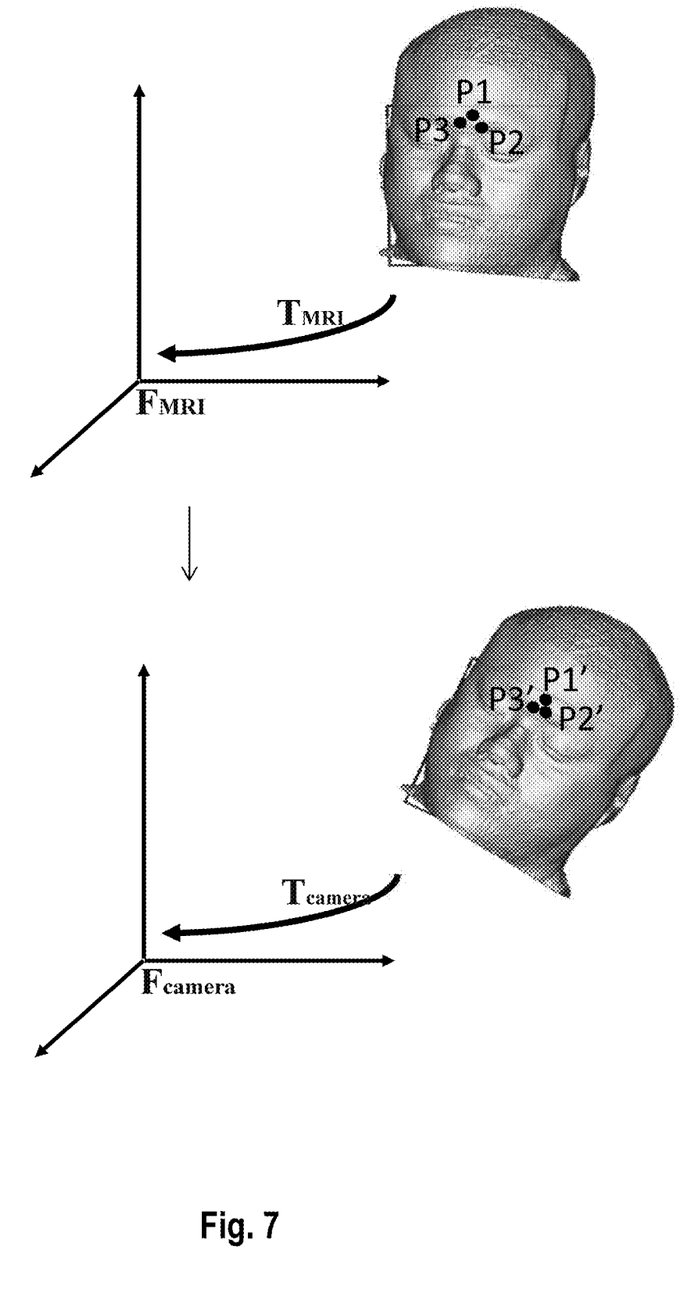
FIG. 7 illustrates an example coordinate transformation from a constructed three-dimensional model coordinate system to a three-dimensional camera coordinate system.

FIG. 7 illustrates an example coordinate transformation from the constructed three-dimensional model coordinate system to the three-dimensional camera coordinate system, in accordance with some embodiments of the present disclosure. This figure will be further discussed below in conjunction with FIG. 8.

Figure 8:
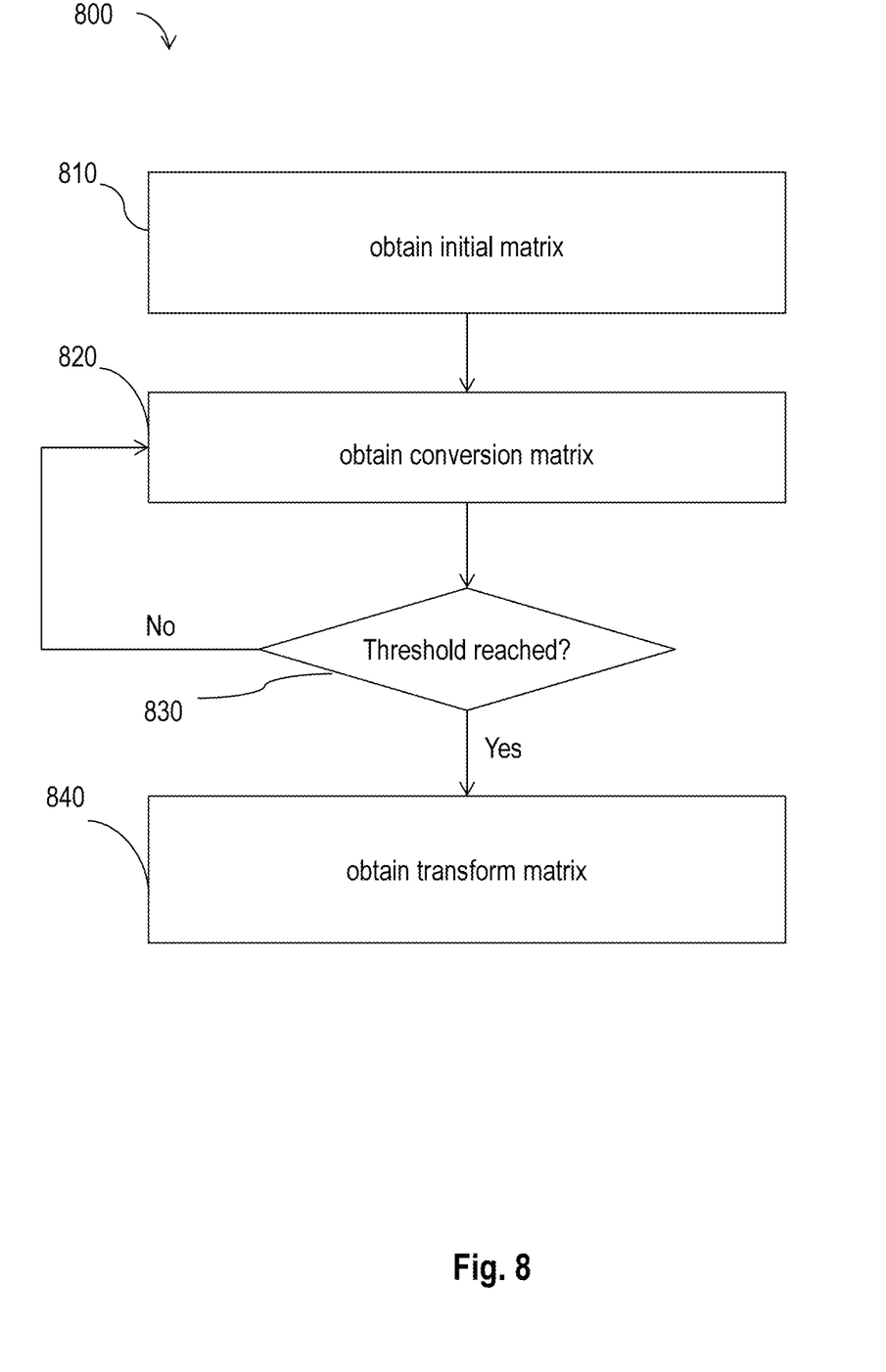
FIG. 8 is a flow diagram illustrating an example process to transform coordinates.

FIG. 8 is a flow diagram illustrating an example process 800 to transform coordinates, in accordance with some embodiments of the present disclosure. Process 800 may include one or more operations, functions, or actions as illustrated by blocks 810, 820, 830, and/or 840, which may be performed by hardware, software and/or firmware. The various blocks are not intended to be limiting to the described embodiments. The outlined steps and operations are only provided as examples, and some of the steps and operations may be optional, combined into fewer steps and operations, or expanded into additional steps and operations without detracting from the essence of the disclosed embodiments. Although the blocks are illustrated in a sequential order, these blocks may also be performed in parallel, and/or in a different order than those described herein.

In conjunction with FIG. 7, in block 810, initial matrices are obtained. In some embodiments, a first initial matrix $T_{MRI}$ and a second initial matrix $T_{camera}$ are obtained. In some embodiments, $$TMRI = \begin{bmatrix} Vector_{X_x} & Vector_{Y_x} & Vector_{Z_x} & P_{1x} \\ Vector_{X_y} & Vector_{Y_y} & Vector_{Z_y} & P_{1y} \\ Vector_{X_z} & Vector_{Y_z} & Vector_{Z_z} & P_{1z} \\ 0 & 0 & 0 & 1 \end{bmatrix} \quad (1)$$

in which $$\overrightarrow{P_1P_2}_{norm} \times \overrightarrow{P_1P_3}_{norm} = Vector_Y$$

$$\overrightarrow{P_1P_2}_{norm} \times Vector_Y = Vector_Z$$

$$\overrightarrow{P_1P_2}_{norm} = Vector_X$$

$Vector_{Xx}$ is the x component of $Vector_X$, $Vector_{Xy}$ is the y component of $Vector_X$, and $Vector_{Xz}$ is the z component of $Vector_X$. Similarly, $Vector_{yx}$ is the x component of $Vector_y$, $Vector_{yy}$ is the y component of $Vector_y$, and $Vector_{yz}$ is the z component of $Vector_y$. $Vector_{Zx}$ is the x component of $Vector_Z$, $Vector_{Zy}$ is the y component of $Vector_Z$, and $Vector_{Zz}$ is the z component of $Vector_Z$. P1x is the x coordinate of P1, $P1_y$ is the y coordinate of P1, and $P1_z$ is the z coordinate of P1.

In some other embodiments, $$Tcamera = \begin{bmatrix} Vector_{X'_x} & Vector_{Y'_x} & Vector_{Z'_x} & P_{1'x} \\ Vector_{X'_y} & Vector_{Y'_y} & Vector_{Z'_y} & P_{1'y} \\ Vector_{X'_z} & Vector_{Y'_z} & Vector_{Z'_z} & P_{1'z} \\ 0 & 0 & 0 & 1 \end{bmatrix} \quad (2)$$

in which $$\overrightarrow{P_{1'}P_{2'}}_{norm} \times \overrightarrow{P_{1'}P_{3'}}_{norm} = Vector_{Y'}$$

$$\overrightarrow{P_{1'}P_{2'}}_{norm} \times Vector_{Y'} = Vector_{Z'}$$

$$\overrightarrow{P_{1'}P_{2'}}_{norm} = Vector_{X'}$$

$Vector_{X'x}$ is the x component of $Vector_{X'}$, $Vector_{X'y}$ is the y component of $Vector_{X'}$, and $Vector_{X'z}$ is the z component of $Vector_{X'}$. Similarly, $Vector_{y'x}$ is the x component of $Vector_{y'}$, $Vector_{y'y}$ is the y component of $Vector_{y'}$, and $Vector_{y'z}$ is the z component of $Vector_{y'}$. $Vector_{Z'x}$ is the x component of $Vector_{Z'}$, $Vector_{Z'y}$ is the y component of $Vector_{Z'}$, and $Vector_{Z'z}$ is the z component of $Vector_{Z'}$. P1'x is the x coordinate of P1', $P1'_y$ is the y coordinate of P1', and $P1'_z$ is the z coordinate of P1'.

Block 810 may be followed by block 820, "obtain conversion matrix." In some embodiments, the conversion matrix may be $T_{camera} T_{MRI}^{-1}$ and P1, P2, and P3 are transformed to the three-dimensional camera coordinate system according to $T_{camera} T_{MRI}^{-1}$. Assuming P1, P2, and P3 are transformed to $P1_{transformed}$, $P2_{transformed}$, and $P3_{transformed}$, respectively, a distance metric associated with differences between $P1_{transformed}$ and P1', $P2_{transformed}$ and P2', and $P3_{transformed}$ and P3' is calculated based on some feasible ICP approaches.

Block 820 may be followed by block 830. In block 830, whether the change of the distance metric reaches a threshold is determined. If the threshold is not reached, block 830 may go back to block 820 in which $P1_{transformed}$, $P2_{transformed}$, and $P3_{transformed}$ are selected to update $T_{camera}$ and eventually obtain new conversion matrix $T_{camera} T_{MRI}^{-1}$. If the threshold is reached, block 830 may be followed by block 840.

In block 840, a transform matrix is obtained to transform points from the three-dimensional camera coordinate system to the robotic arm coordinate system. In some embodiments, the transform matrix $$T_{robot} = \begin{bmatrix} & & & P_{c_x} \\ & R & & P_{c_y} \\ & & & P_{c_z} \\ 0 & 0 & 0 & 1 \end{bmatrix} \quad (5)$$

in which $$R = I + (\sin\theta)K + (1 - \cos\theta)K^2 \quad (4)$$

$$K = \begin{bmatrix} 0 & -\frac{k_z}{|\vec{k}|} & \frac{k_y}{|\vec{k}|} \\ \frac{k_z}{|\vec{k}|} & 0 & -\frac{k_x}{|\vec{k}|} \\ -\frac{k_y}{|\vec{k}|} & \frac{k_x}{|\vec{k}|} & 0 \end{bmatrix}$$

$$\theta = |\vec{k}|$$

$$I = \begin{bmatrix} 1 & 0 & 0 \\ 0 & 1 & 0 \\ 0 & 0 & 1 \end{bmatrix}$$

$\vec{k}$ is a rotation vector associated with a camera center (e.g., origin of the camera coordinate system) in the robotic arm coordinate system;

kx is the x component of $\vec{k}$, ky is the y component of $\vec{k}$, and kz is the z component of $\vec{k}$; and Pcx is the x coordinate of the camera center, Pcy is the y coordinate of the camera center, and Pcz is the z coordinate of the camera center in the robotic arm coordinate system. In some embodiments, example approaches to register the camera center in the robotic arm coordinate system will be further described below in conjunction with FIG. 9.

According to the transform matrix, points on the operation pathway in the three-dimensional model coordinate system may be transformed to the robotic arm coordinate system. Therefore, the robotic arm may move to one or more points on the operation pathway.

Figure 9:
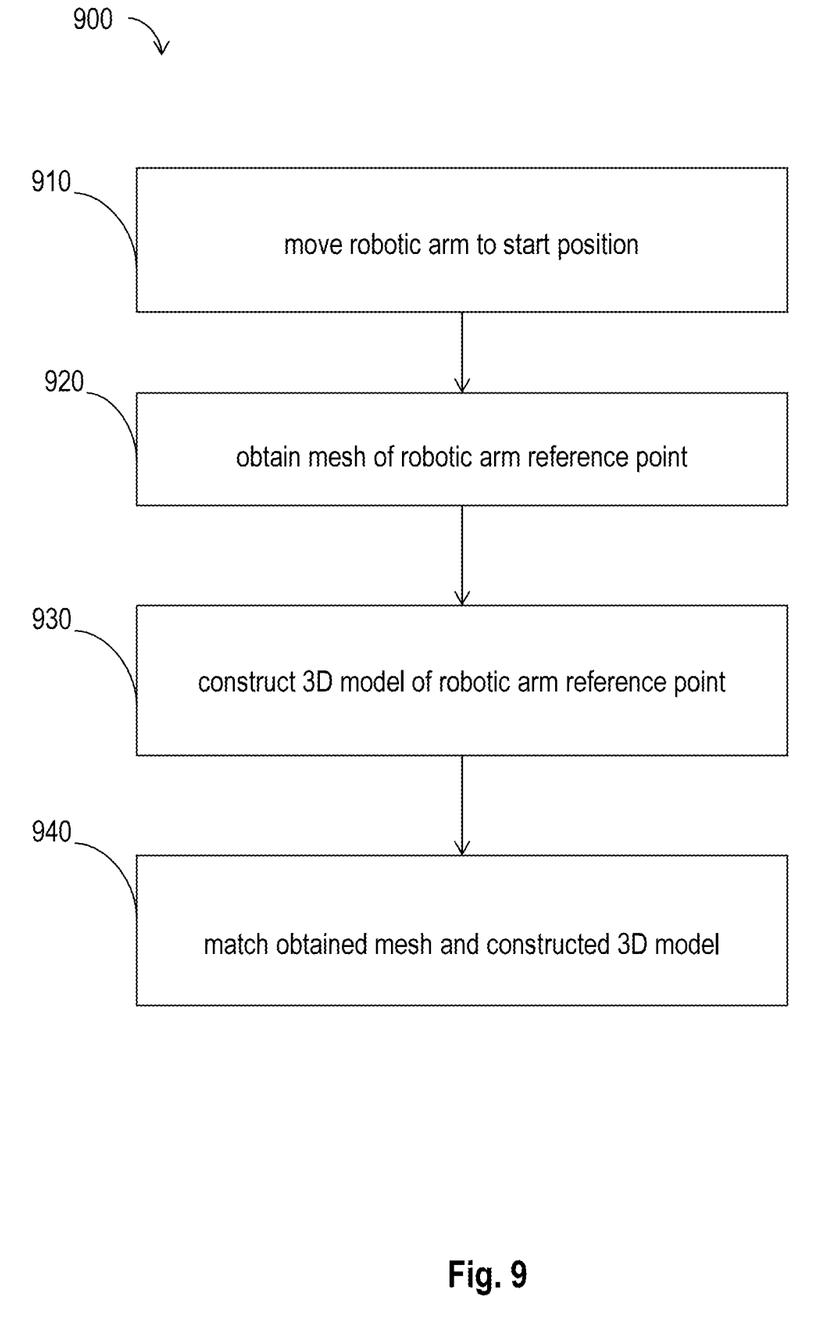
FIG. 9 is a flow diagram illustrating an example process to register an optical device in a robotic arm coordinate system, all arranged in accordance with some embodiments of the present disclosure.

In some embodiments, FIG. 9 is a flow diagram illustrating an example process 900 to register an optical device (e.g., camera) in the robotic arm coordinate system. In some embodiments, the optical device may be mounted at a flange of the robotic arm. To describe the optical device in the robotic arm coordinate system with kx, ky, kz, Pcx, Pcy, and Pcz as set forth above, a point associated with the optical device (e.g., origin of the camera coordinate system) may be registered in the robotic arm coordinate system first according to process 900. Process 900 may include one or more operations, functions, or actions as illustrated by blocks 910, 920, 930 and/or 940, which may be performed by hardware, software and/or firmware. The various blocks are not intended to be limiting to the described embodiments. The outlined steps and operations are only provided as examples, and some of the steps and operations may be optional, combined into fewer steps and operations, or expanded into additional steps and operations without detracting from the essence of the disclosed embodiments. Although the blocks are illustrated in a sequential order, these blocks may also be performed in parallel, and/or in a different order than those described herein.

Process 900 may begin with block 910. In block 910, the robotic arm is configured to move to a start position. In some embodiments, the start position is adjacent to and facing a reference point (e.g., robotic arm base) of the robotic arm. In some embodiments, at the start position, the optical device is configured to capture one or more images of the reference point of the robotic arm. The captured images are associated with spatial relationships between a point of the optical device and the reference point of the robotic arm.

Block 910 may be followed by block 920. In block 920, a mesh of the reference point of the robotic arm is obtained based on the captured images.

Block 920 may be followed by block 930. In block 930, a three-dimensional model of the reference point of the robotic arm is constructed based on certain physical information of the robotic arm. In some embodiments, the physical information may include the dimension, orientation and/or geometric features of the elements of the robotic arm.

Block 930 may be followed by block 940. In block 940, the obtained mesh and the constructed three-dimensional model are matched. Some technical feasible approaches may be used for the matching, for example, iterative closest points approach may be used to match points of the obtained mesh and points of the constructed three-dimensional model to satisfy a given convergence precision. In response to the given convergence precision is satisfied, the spatial relationships between the point of the optical device and the reference point of the robotic arm can be calculated. Based on the calculation, the point of the camera may be registered in and transformed to the robotic arm coordinate system.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

We claim:

1. A system to determine an operation pathway for a patient, comprising:
   a processor; and
   a non-transitory computer-readable medium having stored thereon program code that, upon being executed by the processor, causes the processor to:
   construct a three-dimensional model based on a medical image scan of the patient;
   obtain image information of the patient with a set of two-dimensional optical devices;
   select a first set of two-dimensional feature points associated with the three-dimensional model;
   select a second set of two-dimensional feature points associated with the image information of the patient;
   transform the first set of two-dimensional feature points to a first set of three-dimensional feature points;
   transform the second set of two-dimensional feature points to a second set of three-dimensional feature points;
   match between the first set of three-dimensional feature points and the second set of three-dimensional feature points to determine a relationship that aligns the first set of three-dimensional feature points and the second set of three-dimensional feature points;
   transform coordinates from a first coordinate system associated with the three-dimensional model to a second coordinate system associated with the set of two-dimensional optical devices based on the relationship; and
   determine the operation pathway in a third coordinate system associated with a robotic arm based on the transformed coordinates in the second coordinate system;
   wherein the program code, upon being executed by the processor, causes the processor further to generate a two-dimensional snapshot of the three-dimensional model and select the first set of two-dimensional feature points in the snapshot.

2. The system of claim 1, wherein transforming the first set of two-dimensional feature points to the first set of three-dimensional feature points is based on a reverse operation associated with the snapshot.

3. The system of claim 1, wherein the image information of the patient includes two-dimensional image information of the patient and a depth information associated with the patient.

4. The system of claim 3, wherein the second set of two-dimensional feature points is selected in the two-dimensional image information of the patient.

5. The system of claim 4, wherein transforming the second set of two-dimensional feature points to the second set of three-dimensional feature points is based on the depth information.

6. A method to determine an operation pathway for a patient, comprising:
constructing a three-dimensional model based on a medical image scan of the patient;
obtaining image information of the patient with a set of two-dimensional optical devices;
selecting a first set of two-dimensional feature points associated with the three-dimensional model;
selecting a second set of two-dimensional feature points associated with the image information of the patient;
transforming the first set of two-dimensional feature points to a first set of three-dimensional feature points;
transforming the second set of two-dimensional feature points to a second set of three-dimensional feature points;
matching between the first set of three-dimensional feature points and the second set of three-dimensional feature points to determine a relationship that aligns the first set of three-dimensional feature points and the second set of three-dimensional feature points;
transforming coordinates from a first coordinate system associated with the three-dimensional model to a second coordinate system associated with the set of two-dimensional optical devices based on the relationship;
determining the operation pathway in a third coordinate system associated with a robotic arm based on the transformed coordinates in the second coordinate system;
generating a two-dimensional snapshot of the three-dimensional model; and
selecting the first set of two-dimensional feature points in the snapshot.

7. The method of claim 6, wherein transforming the first set of two-dimensional feature points to the first set of three-dimensional feature points is based on a reverse operation associated with the snapshot.

8. The method of claim 6, wherein the image information of the patient includes two-dimensional image information of the patient and a depth information associated with the patient.

9. The method of claim 8, wherein the second set of two-dimensional feature points is selected in the two-dimensional image information of the patient.

10. The method of claim 9, wherein transforming the second set of two-dimensional feature points to the second set of three-dimensional feature points is based on the depth information.

11. The method of claim 6, wherein any of the first set of two-dimensional feature points and the second set of two-dimensional feature points is substantially planar on a face of the patient.

12. A non-transitory computer-readable storage medium that includes a set of instructions which, in response to execution by a processor, cause the processor to perform a method to determine an operation pathway for a patient, wherein the method comprises:
constructing a three-dimensional model based on a medical image scan of the patient;
obtaining image information of the patient with a set of two-dimensional optical devices;
selecting a first set of two-dimensional feature points associated with the three-dimensional model;
selecting a second set of two-dimensional feature points associated with the image information of the patient;
transforming the first set of two-dimensional feature points to a first set of three-dimensional feature points;
transforming the second set of two-dimensional feature points to a second set of three-dimensional feature points;
matching between the first set of three-dimensional feature points and the second set of three-dimensional feature points to determine a relationship that aligns the first set of three-dimensional feature points and the second set of three-dimensional feature points;
transforming coordinates from a first coordinate system associated with the three-dimensional model to a second coordinate system associated with the set of two-dimensional optical devices based on the relationship;
determining the operation pathway in a third coordinate system associated with a robotic arm based on the transformed coordinates in the second coordinate system;
generating a two-dimensional snapshot of the three-dimensional model; and
selecting the first set of two-dimensional feature points in the snapshot.

13. The non-transitory computer-readable storage medium of claim 12, wherein transforming the first set of two-dimensional feature points to the first set of three-dimensional feature points is based on a reverse operation associated with the snapshot.

14. The non-transitory computer-readable storage medium of claim 12, wherein the image information of the patient includes two-dimensional image information of the patient and a depth information associated with the patient.

15. The non-transitory computer-readable storage medium of claim 14, wherein the second set of two-dimensional feature points is selected in the two-dimensional image information of the patient.

16. The non-transitory computer-readable storage medium of claim 15, wherein transforming the second set of two-dimensional feature points to the second set of three-dimensional feature points is based on the depth information.

* * * * *